(12) United States Patent
Stiehl et al.

(10) Patent No.: US 8,721,595 B2
(45) Date of Patent: May 13, 2014

(54) SURGICAL SUCTION WAND

(75) Inventors: James B. Stiehl, Salem, IL (US); Kurt R. Stiehl, San Jose, CA (US)

(73) Assignee: Stiehl Technologies, LLC, Salem, IL (US)

( * ) Notice: Subject to any disclaimer, the term of this patent is extended or adjusted under 35 U.S.C. 154(b) by 27 days.

(21) Appl. No.: 13/469,765

(22) Filed: May 11, 2012

(65) Prior Publication Data

US 2013/0304003 A1  Nov. 14, 2013

(51) Int. Cl.
*A61M 1/00* (2006.01)

(52) U.S. Cl.
USPC ........... 604/119; 604/317; 604/318; 604/320; 604/321; 604/322; 604/323; 604/324; 604/325; 604/326; 604/327; 604/328; 604/329; 604/330; 604/331; 604/349

(58) Field of Classification Search
USPC .......................... 604/317, 318, 319, 320, 321
See application file for complete search history.

(56) References Cited

U.S. PATENT DOCUMENTS

| | | | |
|---|---|---|---|
| 1,889,425 A | 11/1932 | Sorensen | |
| 4,068,664 A | 1/1978 | Sharp et al. | |
| 4,193,406 A | 3/1980 | Jinotti | |
| 4,215,476 A | 8/1980 | Armstrong | |
| 4,299,221 A | 11/1981 | Phillips et al. | |
| 4,400,158 A | 8/1983 | Garcia | |
| 4,468,217 A | 8/1984 | Kuzmick et al. | |
| 4,519,385 A | 5/1985 | Atkinson et al. | |
| 4,526,573 A | 7/1985 | Lester et al. | |
| 4,589,869 A | 5/1986 | Wernborg | |
| 4,708,717 A | 11/1987 | Deane et al. | |
| 5,100,377 A | 3/1992 | Freitas et al. | |
| 5,254,085 A | 10/1993 | Cleveland, Jr. | |
| 5,269,785 A | 12/1993 | Bonutti | |
| 5,520,667 A | 5/1996 | Roche | |
| 5,520,668 A | 5/1996 | Greff et al. | |
| 5,554,111 A * | 9/1996 | Morrey et al. | 604/26 |
| 5,704,909 A | 1/1998 | Morrey et al. | |
| 5,779,649 A | 7/1998 | Herbert | |
| 5,807,313 A | 9/1998 | Delk et al. | |
| 5,807,353 A | 9/1998 | Schmitz | |
| 6,193,672 B1 | 2/2001 | Clement | |
| 6,200,292 B1 | 3/2001 | French et al. | |
| 6,406,471 B1 | 6/2002 | Jang et al. | |
| 6,540,713 B1 | 4/2003 | Cimino | |
| 6,783,532 B2 | 8/2004 | Steiner et al. | |
| 7,588,033 B2 | 9/2009 | Wondka | |

(Continued)

FOREIGN PATENT DOCUMENTS

| | | |
|---|---|---|
| GB | 2367750 | 4/2002 |
| WO | 2011/056946 A1 | 5/2011 |

OTHER PUBLICATIONS

International Search Report, PCT/US2010/055413, dated Jan. 6, 2011, 3 pages.
Written Opinion, PCT/US2010/055413, dated Jan. 6, 2011, 7 pages.

(Continued)

*Primary Examiner* — Tatyana Zalukaeva
*Assistant Examiner* — Ilya Treyger
(74) *Attorney, Agent, or Firm* — Senniger Powers LLP (57) ABSTRACT

A suction wand for use during a surgical operation involving cutting of bone which yields bone debris, the wand comprising a suction conduit, a suction tip, and a positive pressure conduit for directing gas toward the suction tip to expel debris.

11 Claims, 12 Drawing Sheets

(56) References Cited

U.S. PATENT DOCUMENTS

| | | |
|---|---|---|
| 7,611,473 B2 | 11/2009 | Boock et al. |
| 2002/0178696 A1 | 12/2002 | Korff |
| 2004/0122447 A1 | 6/2004 | Harmon et al. |
| 2005/0189288 A1 | 9/2005 | Hershberger et al. |
| 2006/0058730 A1 | 3/2006 | Pratt et al. |
| 2006/0155260 A1 | 7/2006 | Blott et al. |
| 2007/0213667 A1 | 9/2007 | Prusmack |
| 2008/0154183 A1 | 6/2008 | Baker et al. |
| 2008/0200877 A1 | 8/2008 | Panotopoulos |
| 2009/0306669 A1 | 12/2009 | Takahashi |
| 2010/0190133 A1 | 7/2010 | Martinez |
| 2011/0112515 A1 | 5/2011 | Stiehl et al. |
| 2013/0123721 A1 | 5/2013 | Stiehl et al. |

OTHER PUBLICATIONS

Non-Final Office Action, U.S. Appl. No. 13/470,008, dated Oct. 3, 2013.

Non-Final Office Action, U.S. Appl. No. 12/939,496, dated Oct. 4, 2013.

Amendment G, filed on Dec. 31, 2013, in U.S. Appl. No. 12/939,496, 23 pages.

Amendment A, filed on Dec. 31, 2013, in U.S. Appl. No. 13/470,008, 26 pages.

* cited by examiner

SURGICAL SUCTION WAND

FIELD OF THE INVENTION

The present invention generally relates to a suction device for use in surgical procedures and more particularly to a surgical suction device for removing debris from a surgery site.

BACKGROUND OF THE INVENTION

Suction devices are commonly used in a variety of medical applications to evacuate various fluids from a patient for a variety of purposes. For example, during surgery, blood and other body fluids are commonly removed to permit visual inspection of the surgical site and disposal of fluids. Suction wands may also provide for the production of positive pressure (usually air or water) to irrigate the surgical site. One such example is disclosed in Lester, U.S. Pat. No. 4,526,573 which shows a suction conduit for sucking debris away from the surgery site and an irrigation conduit for directing irrigation fluid to a surgery site.

Prusmack US Publication No. 2007/0213667 discloses a suction irrigation cleaner configured to apply negative air pressure by connecting a first port to a suction source for removing debris and fluid from a surgical site. There is also an irrigation/positive pressure line to deliver positive air/vapor pressure by connecting a second port to a positive pressure source. The positive pressure fluid is used for irrigation and alternatively to unclog the device if tissue or clot is sucked into the device. The apparatus disclosed in Prusmack is not ideal because the tissue and clot can travel through device all the way to the valve mechanisms, potentially damaging the device. The irrigation function is complicated as it requires both turning of a stopcock and operation of a button to move the irrigation channel into the main flow path. Also, it does not inhibit larger potentially clogging debris from being sucked into the device beyond the point where the declogging function can be effective.

Historically, suction wands (commonly referred to as "sucker tips") were fabricated from metal and were reusable only after suitable cleaning and sterilization. With the recent advent of disposable surgical equipment, however, metal suction wands have been almost entirely replaced by cheaper, light weight, disposable suction wand systems fabricated from plastics.

In orthopedic surgery, suction wands are vital for keeping the surgical site 'dry' improving visualization of tissues and for recovery of lost blood through means of 'cell savers' or devices that allow for the re-infusion of blood that may have oozed from the tissues of the surgical site. As shown in the Prusmack publication, a major obstacle to the optimal performance of sucker wands is the obstruction that occurs when bone bits and other debris are sucked into the suction line, effectively clogging the egress of fluids away from the surgical site and blocking the suction. A secondary problem has been the relatively high flow of air through the wand during the surgical procedure which leads to the potential deposition of airborne bacteria on the tip of the wand. And because the wand tip is moistened by the egress of fluid during suction, the wand tends to attract dust or debris which are then expelled to the surgical site when positive pressure is produced. Studies have shown that a sucker wand may be one of the highest sources of contamination during a surgical procedure.

Therefore, there exists a need for a suction wand device that allows for the egress of fluids being removed from a surgical site, but still provides the operator the ability to conveniently unclog or unplug the device without the fear of contaminating the surgical site or damaging the device. The present invention also offers an efficient design that can be constructed with disposable plastic materials and easily disassembled for cleaning purposes.

SUMMARY OF THE INVENTION

Briefly, therefore, the invention is directed to a suction wand for use in aspirating a surgical site during a surgical operation involving cutting of tissue which yields debris, the suction wand comprising a handle, a head portion attached to the handle at a connection, wherein the head portion comprises a tubular member, a suction conduit at least partially disposed in the head portion and partially defining a suction path, a suction tip at a free end of the suction conduit remote from the handle, wherein the suction path extends from the suction tip to a vacuum source end of the suction path remote from the suction tip, a filter screen for retaining debris, wherein the filter screen comprises a surface with holes perforated therein and is disposed in the suction path at the suction tip and has a first side facing a tip direction and an opposite second side facing a vacuum source direction, a positive pressure conduit in the head portion through which fluid flows and is directed into the suction conduit in a direction toward the tip such that fluid flows in the tip direction for expelling debris from the tip, and a conduit valve operable between an open position in which fluid flows through the positive pressure conduit and into the suction conduit toward the suction tip and a closed position in which fluid does not flow into the suction conduit.

Other objects and features will be in part apparent and in part pointed out hereinafter.

BRIEF DESCRIPTION OF THE DRAWINGS

Corresponding reference characters indicate corresponding parts throughout the drawings.

DESCRIPTION OF THE PREFERRED EMBODIMENTS

Figure 1:
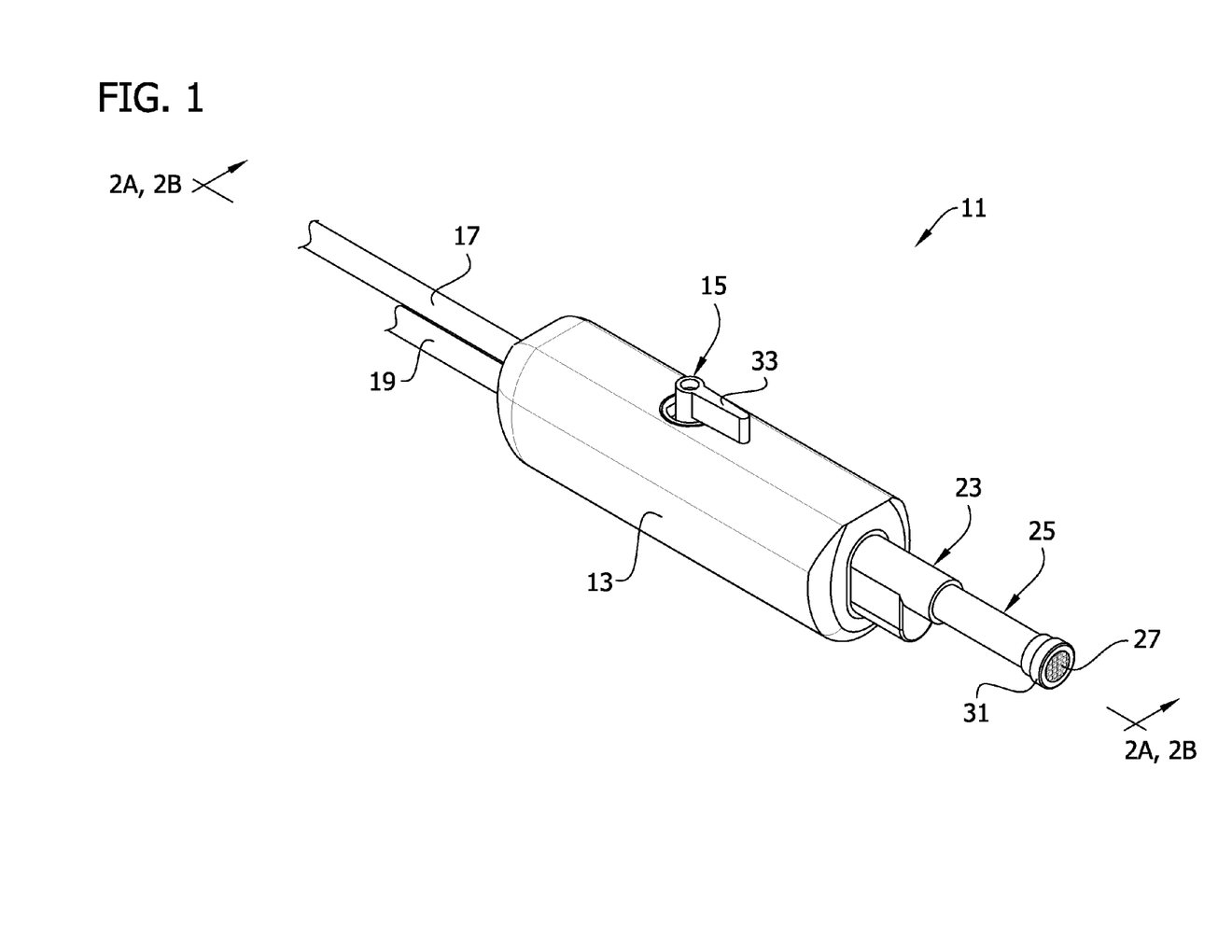
FIG. 1 is a perspective of a suction wand of the present invention.

Referring to the illustrated embodiment, and in particular FIG. 1, a suction wand for use during surgical operation to aspirate a surgical site is generally indicated at 11. The suction wand comprises a handle 13 and a valve generally indicated at 15, partially received in the handle for movement between an open and a closed position. An inflow tube 17 extends proximally from a proximal end of the handle 13 and is configured for attachment to a positive pressure source (not shown). The preferred positive pressure source is a $CO_2$ tank or a line source. An outflow tube 19, below the inflow tube 17, also extends proximally from the proximal end of the handle 13 and is configured for attachment to a negative pressure or suction source (not shown).

A mount 21 (FIGS. 2A-B) at a distal end of the handle 13 attaches a connector 23 and head portion 25 to the handle. The head portion 25 comprises a tubular member having a filter screen 27 disposed in an open, distal end or tip 29 of the head portion. A cap 31 retains the filter screen 27 in the tip 29. The cap 31 can be removable to allow for the replacement of the filter screen 27 after use. As will be explained in greater detail below, when the valve 15 is in the closed position (FIG. 2A), activation of the suction source will generate a negative pressure gradient at the tip 29 of the head portion 25 for aspirating the surgical site when the wand 11 is used in a surgical procedure. Movement of an actuator 33 of the valve 15 moves the valve from the closed position to the open position (FIG. 2B), permitting fluid from the positive pressure source to escape through the tip 29 of the head portion 25, past the filter screen 27 to expel any debris collected on the screen during aspiration. In the illustrated embodiment, the valve 15 is a ball valve. The handle 13, mount 21, connector 23, head portion 25 and cap 31 are formed from plastic. Lubricity agents and surface treatments as are well known in the art may be used to enhance flow within the plastic. Alternatively, the components can be made from other suitable materials such as stainless steel.

Figure 2A:
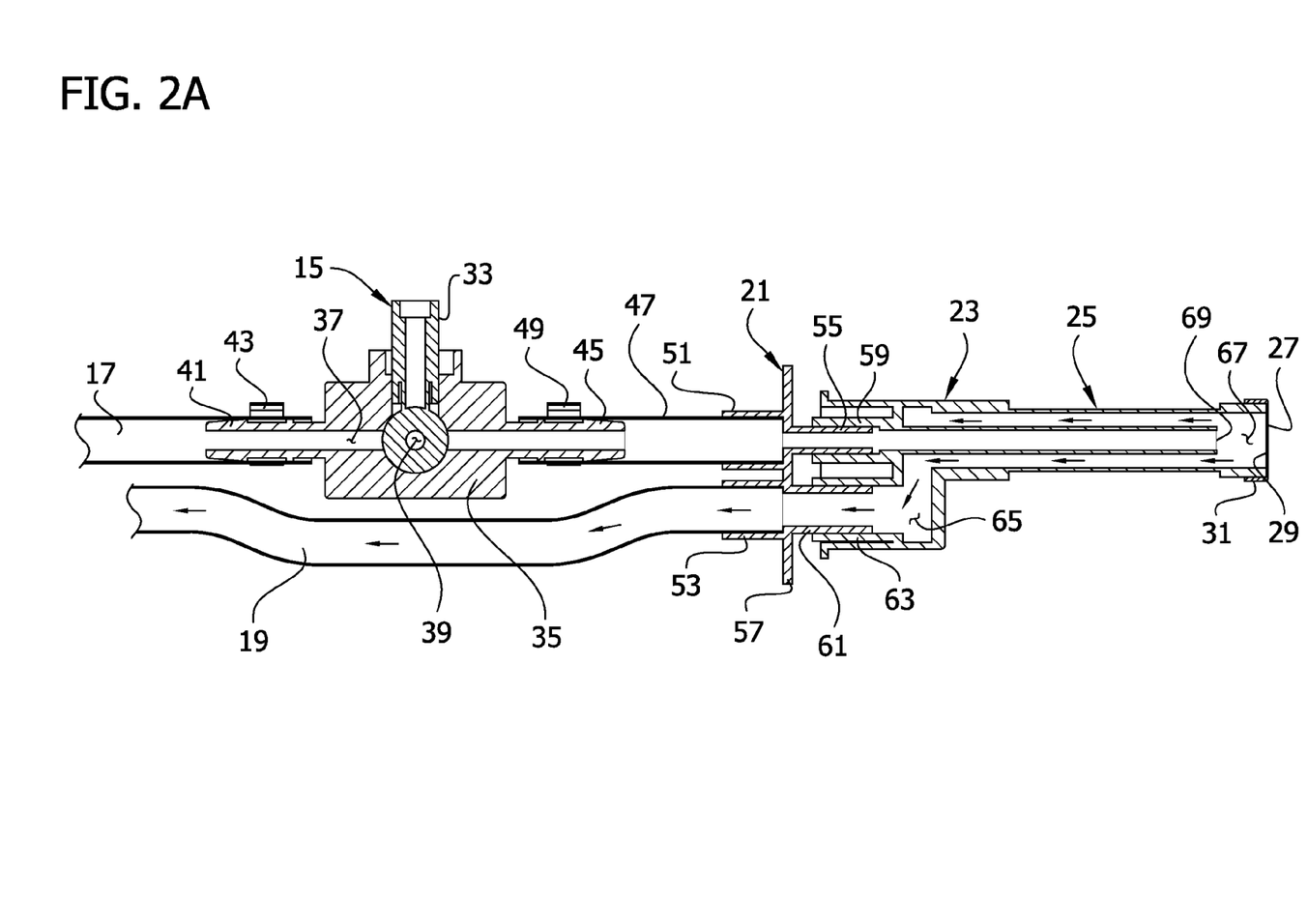
FIG. 2A is a cross-section of the suction wand taken through line 2A,2B-2A,2B in FIG. 1 with a handle removed and showing a valve of the wand in a closed position.
Figure 2B:
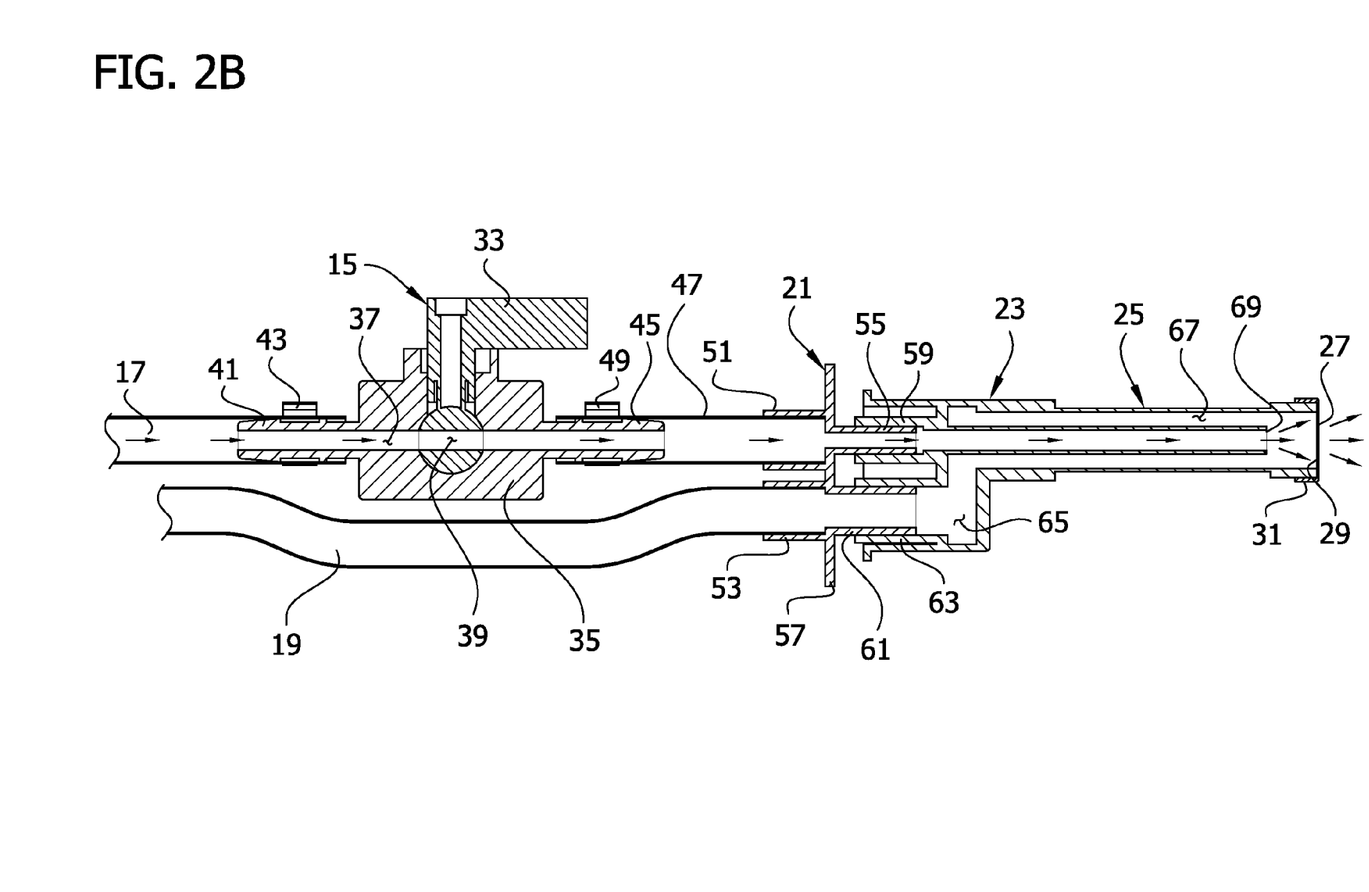
FIG. 2B is a cross section of the suction wand taken through line 2A,2B-2A,2B in FIG. 1 with the handle removed and showing the valve in an open position.

Referring to FIGS. 2A and 2B, a valve housing 35 is disposed in the handle 13 and seats the valve 15 for pivotal movement in the valve housing between the open and closed positions. The valve housing 35 includes a valve passage 37 that extends longitudinally in the valve housing and is partially defined by an opening 39 in the valve 15. An inlet port 41 extends proximally from a proximal end of the valve housing 35 and is received in a distal end of the inflow tube 17 to fluidly connect the inflow tube to the valve passage 37. A clamp 43 secures the inflow tube 17 around the inlet port 41. An outlet port 45 extends distally from a distal end of the valve housing 35 and is received in a proximal end of a connection tube 47 to fluidly connect the connection tube to the valve passage 37. A clamp 49 secures the connection tube 47 around the outlet port 45. A distal end of the connection tube 47 is received in a first connection port 51 of the mount 21 to fluidly connect the connection tube to the mount. A second connection port 53 of the mount 21, below the first connection port 51, receives a distal end of the outflow tube 19 to fluidly connect the outflow tube to the mount. In the illustrated embodiment, the connection tube 47 and outflow tube 19 are secured in the connection ports 51, 53, respectively, by adhesive. However, other suitable connection means such as clamps or by friction fit are within the scope of the present invention. Also, connectors other than clamps 43, 49 can be used.

A first mount port 55 extends distally from a base 57 of the mount 21 and is received in a first connector port 59 of the connector 23 to fluidly connect the first mount port to the connector. A second mount port 61 of the mount 21, below the first mount port 55, also extends distally from the base 57 and is receive in a second connector port 63 of the connector 23 to fluidly connect the second mount port to the connector.

Figure 3:
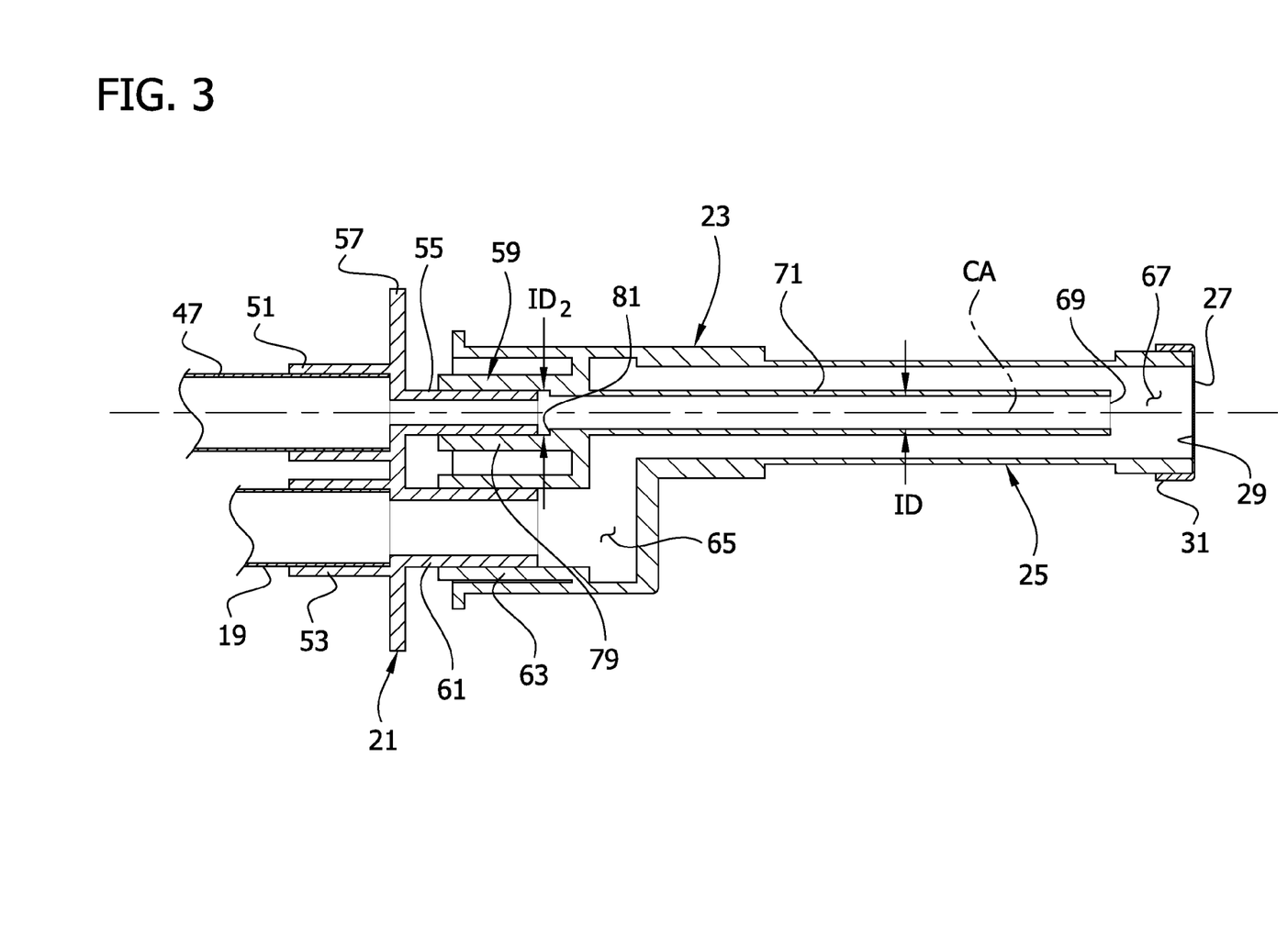
FIG. 3 is an enlarged fragmentary cross section showing a suction conduit and a positive pressure conduit of the wand.

The first connector port 59 extends distally through the connector 23 into the head portion 25. The first mount port 55 and first connector port 59 broadly define a positive pressure conduit. The second connector port 63 opens into an interior space 65 in the connector 23 which opens into an interior space 67 in the head portion 25. The second mount port 61, second connector port 63, connector interior space 65 and head portion interior space 67 broadly define a suction conduit. The suction conduit extends around the positive pressure conduit to the tip 29 of the head portion 25. In this embodiment the longitudinal axes of the suction conduit and positive pressure conduit are coincident such that they are disposed on a common central axis CA (FIG. 3). In the illustrated embodiment, an open end or tip 69 of the positive pressure conduit is spaced between about ¼ and about ¾ in., e.g., about ½ in., from the filter screen 27, the reasons for which will be explained in greater detail below. It is seen there that in once sense the central axis of the positive pressure conduit, which here is the $CO_2$ gas conduit, and in particular the segment of the conduit which is the $CO_2$ gas conduit extension, is parallel with the central axis of the suction conduit, at least in the segment from the suction tip back to the handle. In another aspect it is seen that the central axis of the positive pressure conduit, which here is the $CO_2$ gas conduit, and in particular segment of the conduit which is the $CO_2$ gas conduit extension, is coincident with the central axis of the suction conduit, at least in the segment from the suction tip back to the handle.

Referring to FIG. 2A, a suction path is illustrated by a series of arrows. The suction path extends from a distal side of the filter screen 27 past the screen and tip 29 of the head portion 25, through the suction conduit and into the outflow tube 19 to the suction source. When the suction wand 11 is used during a surgical procedure to aspirate a surgical site, the tip 29 of the head portion 25 is placed adjacent the surgical site and fluid and small particles permitted by the filter screen 27 are sucked from the surgical site along the suction path and can be collected remotely from the suction wand. To prevent fluid and debris from entering the positive pressure conduit a grate (not shown) can optionally be placed over the tip 69 of the positive pressure conduit.

Conversely, a positive pressure path is illustrated by a series of arrows in FIG. 2B. The positive pressure path extends from the positive pressure source, through the inflow tube 17, into the inlet port 41 of the valve housing 35, through the valve passage 37, out the outlet port 45, into the connection tube 57, past the first connection port 51 of the mount 21, through the first mount port 55, into the first connector port 59 of the connector 23, through the positive pressure conduit, out the tip 69 of the positive pressure conduit, partially through the interior space 67 of the head portion 25 and out the tip 29 of the head portion, past the filter screen 27. The conduit segment between port 55 and tip 69 constitutes a $CO_2$ gas conduit extension which extends within an interior of the suction conduit for directing $CO_2$ gas directly at the suction tip. The $CO_2$ gas conduit extension in the preferred embodiment shown has a smaller inner diameter than the inner diameter of the $CO_2$ gas main conduit section, as manifest by tubes 47 and 17. After the surgical site has been aspirated, the suction wand 11 can be operated in the positive pressure mode to expel any debris, such as larger bone chips in the case of orthopedic surgery, which may be caught in the filter screen 27. Referring to FIG. 3, a distal end 71 of the first connector port 59 has an inner diameter ID of about 3/32 in. The inner diameter ID of the distal end 71 of the first connector port 59 can be between about 1/16 and about 1/8 in., the purpose of which will be explained in greater detail below.

It can therefore be seen from FIGS. 1-3 that the positive pressure conduit has a longitudinal axis which is coincident with a longitudinal axis of the suction path along a majority of the length of the tubular member of the head portion. In particular, the positive pressure conduit is at least partially disposed in the head portion and partially defining a fluid path. Fluid flows through this positive pressure conduit and is directed into the suction conduit in a direction toward the tip such that fluid flows in the tip direction for expelling debris from the tip. It can be seen that the positive pressure conduit has a longitudinal axis which is coincident or parallel with a longitudinal axis of the suction path along a majority of the length of the tubular member of the head portion. There is a conduit valve operable between an open position in which fluid flows through the positive pressure conduit and into the suction conduit toward the suction tip and a closed position in which fluid does not flow into the suction conduit. These axes—the axis of the positive pressure conduit and of the suction conduit—may alternatively be parallel, rather than coincidental. It is also seen that the positive pressure conduit longitudinal axis is coincident (or alternatively may be parallel) with a longitudinal axis of the tubular member of the head portion from the connection 423 between the handle and the head portion in the tip direction. The suction path, as in the other embodiments, surrounds the positive pressure conduit along a majority of the length of the tubular member of the head portion.

Figure 4:
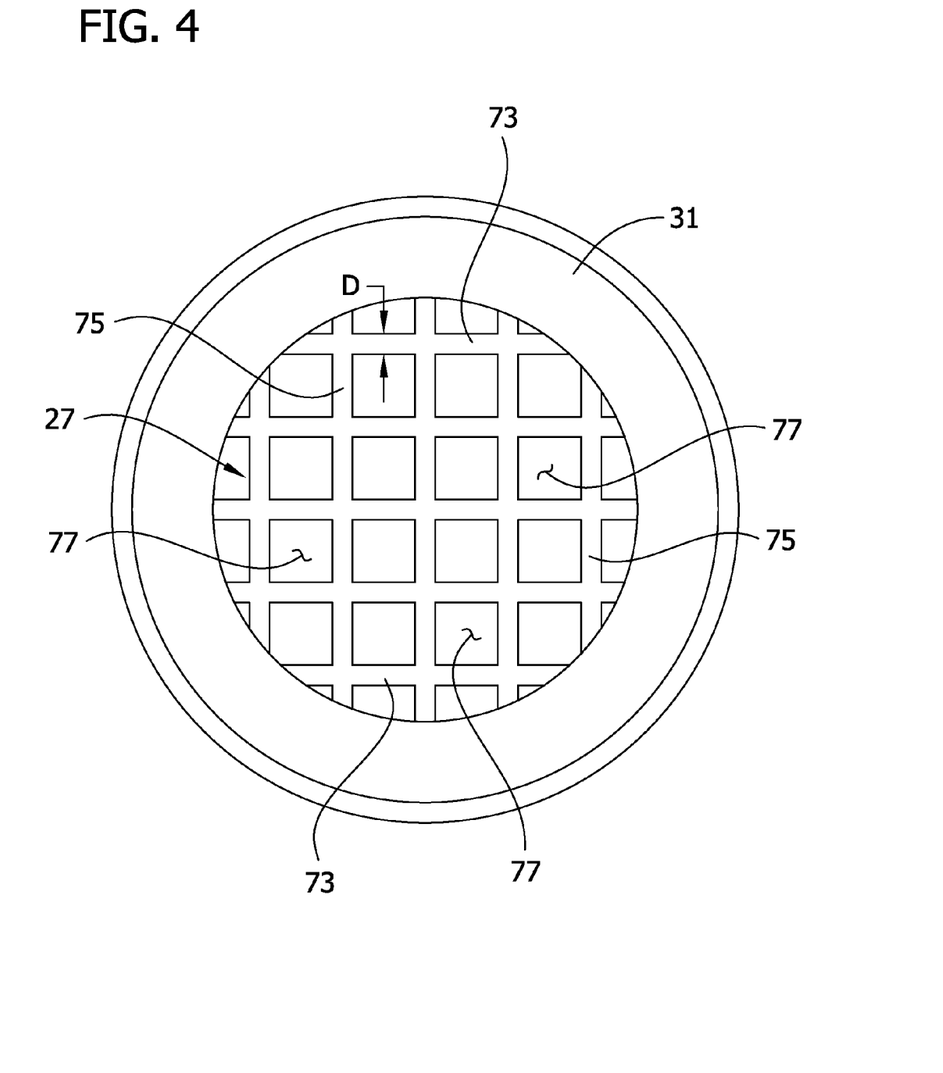
FIG. 4 is an enlarged front view of a filter screen and cap of the suction wand.

Referring to FIG. 4, the filter screen 27 comprises a woven mesh of parallel horizontal wires 73 and parallel vertical wires 75 forming open areas 77. The wires 73, 75 may have a diameter D between about 0.01 in. and about 0.02 in. The wires 73, 75 can be spaced such that there are between about 12 to about 30 open areas 77 per square in. In the illustrated embodiment, there are about 20 open areas 77. The open areas 77 can make up between about 49% and about 54% of the surface area of the filter screen 27. The wires 73, 75 of the filter screen 27 are arranged such that the open areas 77 are sized and spaced to prevent debris from entering the suction conduit during aspiration of a surgical site yet still provide a sufficient opening to deliver a maximum output flow when the wand 11 is in the positive pressure delivery mode. In a preferred embodiment the wires 73, 75 are metal (i.e., steel, copper, brass, platinum). However, the wires 73, 75 can also be made from plastic, nylon or any other suitable material.

Figure 5A:
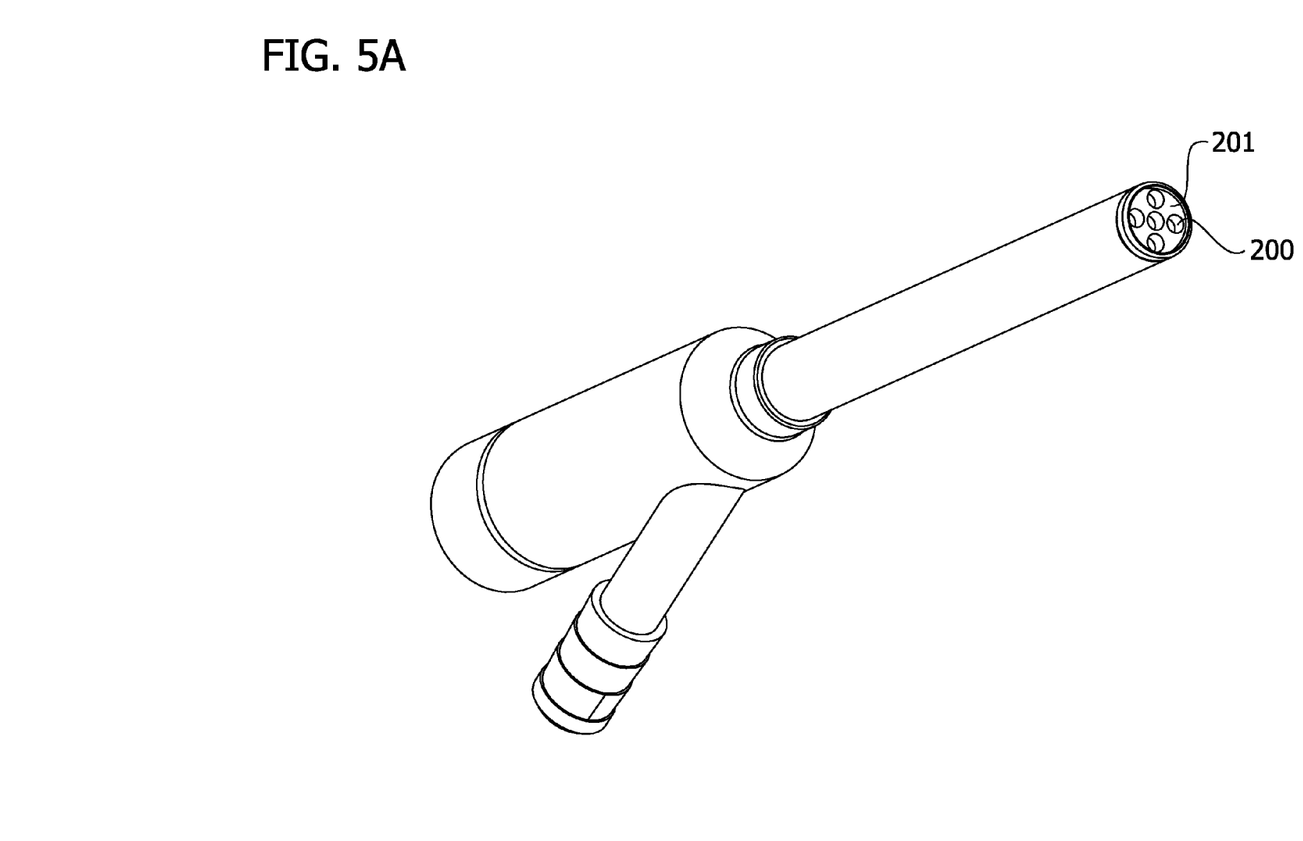
FIG. 5A is a perspective view of an alternative filter screen attached to the wand, with the screen inset slightly, for example by up to 2 millimeters.
Figure 5B:
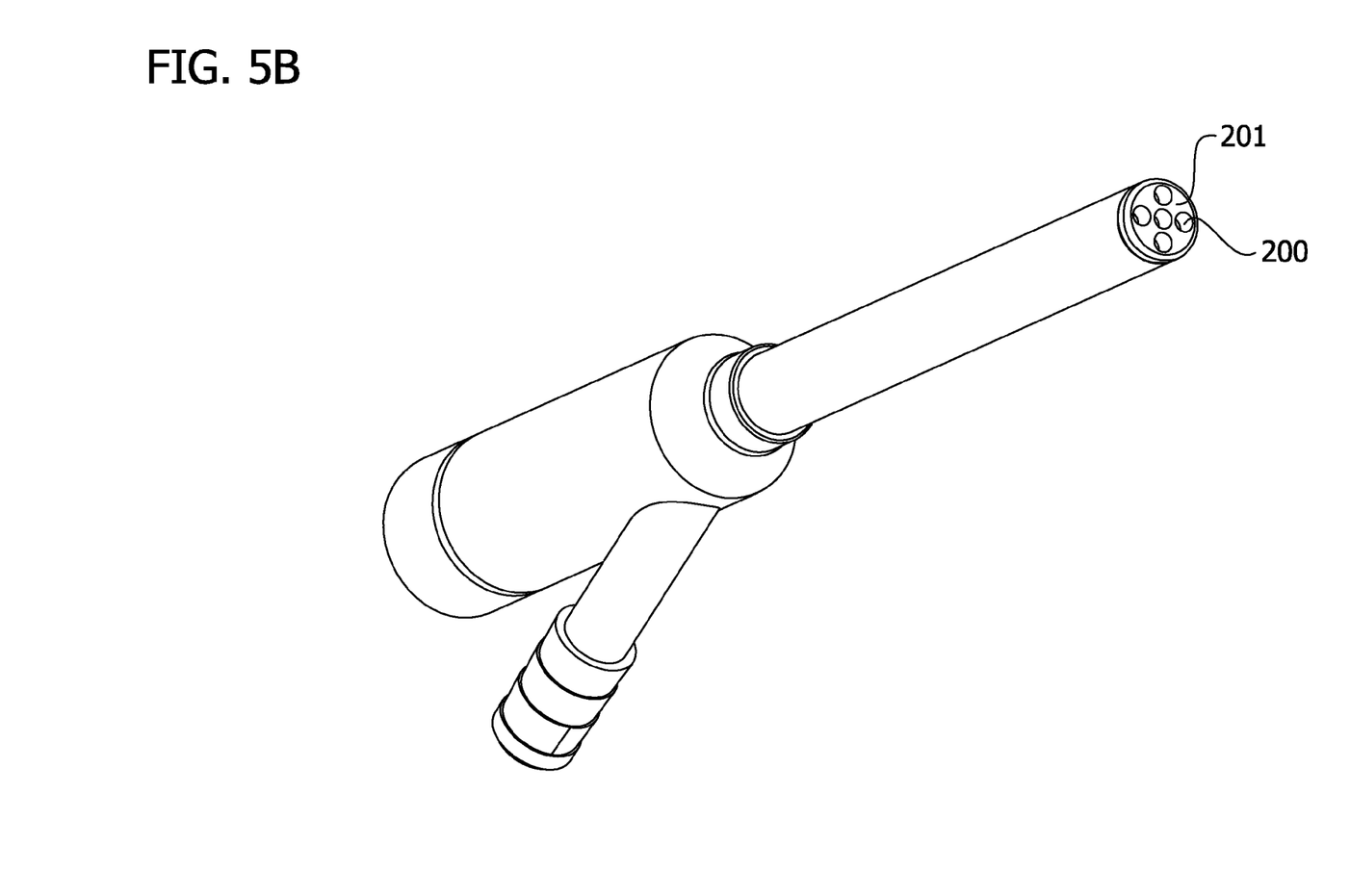
FIG. 5B is a perspective view of a further alternative of the filter screen attached to the wand, with the screen flush with the tip.
Figure 5C:
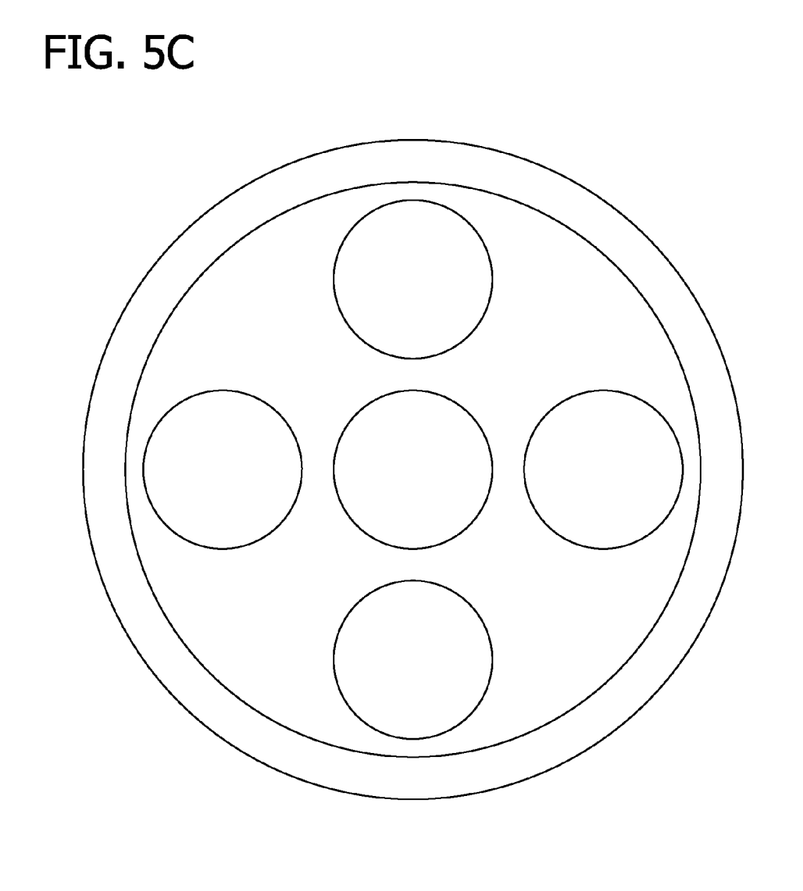
FIG. 5C is a front view of the alternative filter screen.

Referring to FIGS. 5A and 5B, in this embodiment the filter screen comprises a surface with holes 200 perforated therein, such as a metal or plastic plate 201 with holes perforated therein. In the version of this embodiment shown here, the surface is a flat plate about 1/4 to 3/8 inch in diameter and has a plurality of holes which are 5/64 of an inch in diameter. The principle benefit of the metal or plastic screen surface is to allow for the expulsion of organic proteinaceous material which may have a thick gelatinous character. The smooth surface allows this debris to be easily disrupted or brushed away. The plate is a component of a screw tip may be permanently attached such as by welding, brazing, crimping or the like as shown in FIG. 5B. Alternatively, the filter screen may be releasably attached such as by screw attachment onto the suction wand tip. This tip screen may either be flush with the surface or slightly recessed one to two millimeters. A front view of this screen is shown in FIG. 5C.

In one preferred embodiment, the ratio of the total entrance area of the holes to the solid area on the screen is at least 0.2, such as between 0.2 and 0.6, for example, between 0.3 and 0.5; and the ratio of the total entrance area of the holes to the total area (holes plus solid area) is at least 0.4, such as between 0.4 and 1, for example between 0.5 and 0.7. The illustrated embodiment has a hole entrance area of 0.022 in$^2$, a solid area of 0.036 in$^2$, and a total area of 0.058 in$^2$. The ratio of the total entrance area of the holes to the solid area on the screen in this embodiment is 0.38 and the ratio of the total entrance area of the holes to the total area (holes plus solid area) is 0.6.

In another embodiment, the opening at the suction tip constitutes a single slit or other-shaped opening. When a piece of debris to large to fit through the slit or other opening becomes lodged on the outside of the slit or other opening, the positive pressure conduit may be activated to dislodge it, as in the case of dislodgement of debris from a filter screen as described herein.

In use, the inflow tube 75 is preferably connected to a positive pressure source comprising a $CO_2$ tank or line source. Carbon dioxide is preferred because of its safety, surgical compatibility, and availability. Specifically, this relates to the lack of flammability of the $CO_2$ gas, and its property of high solubility and low chance for embolus into the blood stream. Additionally, the relatively small inner diameter ID of the distal end 71 of the first connector port 59 (about 3/32 in.) produces a high gas flow at the tip 29 of the head portion 25. As shown in FIG. 3, a proximal end 79 of the first connector port 59 has an inner diameter $ID_2$ that is greater than the inner diameter ID of the distal end 71 of the first connector port forming a shoulder 81 in the first connector port. This constriction in conduit area, under the Venturi principle, with a $CO_2$ pressure typically at 50 psi dramatically increases the air flow at the tip 29 of the head portion 25. The space between the tip 69 of the positive pressure conduit and the tip 29 of the head portion 29 also controls the pressure at the tip of the head portion. The increase in pipe area that occurs in the transition between the tip 69 of the positive pressure conduit and the tip 29 of the head portion 25 will slightly decrease the pressure seen at the head portion tip. An additional mechanism to guarantee high gas pressure at the tip 29 of the wand 11 is to clamp the outflow tube 19 with a hose clamp (not shown). This will create a closed pressure system. The pressure in the gas source tank (upstream of the regulator) is typically several hundred to several thousand psi. Thus, the gas pressure at the outlet of the pressure regulator, and inlet to the tubing, is the 50 psi described above. Pressure losses occur in all piping systems, due to friction and turbulence in the pipes, fittings, and valves. In general, the longer the pipe and the more valves/fittings, the greater the pressure loss will be. In the case of, for example, tubing which is 10 feet long and where there are several in-line check-valves, a membrane filter, a manual plunger valve, etc., the net effect of these losses is that the pressure at the tip of the nozzle (front the screen) is in the preferred embodiment between about 0.5 and about 2 psi, for example between 0.75 and 1 psi.

Also, because the longitudinal axis of the positive pressure conduit is coincident with the longitudinal axis of the suction conduit, the $CO_2$ blast produced by the positive pressure source will get a "running start" since there are no turns or bends in the $CO_2$ path which could slow down the gas flow. The linear $CO_2$ path also reduces the risk of any "dead spots" that can result from a build up of turbulence at the bends. Finally, the alignment of the positive pressure conduit and suction conduit ensures that the blast of $CO_2$ impacts the filter screen 27 in a directly perpendicular manner.

The high pressure, focused blast of $CO_2$ that results from this construction is needed so that a sufficient amount of gas impinges upon any captured debris in the filter screen 27 to expel the debris. The open areas 77 in the filter screen 27 ensure that a sufficient amount of gas can impinge upon the captured debris to expel the debris from the screen. It was found from clinical experience that the range of about 12 to about 30 open areas 77 per square in. is the preferred range to retain bone chips and fibrous proteinaceous debris large enough to clog the wand 11 while still providing enough open area to produce a high blast of $CO_2$ through the screen 27 to expel the debris, and enough open area to provide the desired suction in normal operation.

Figure 6:
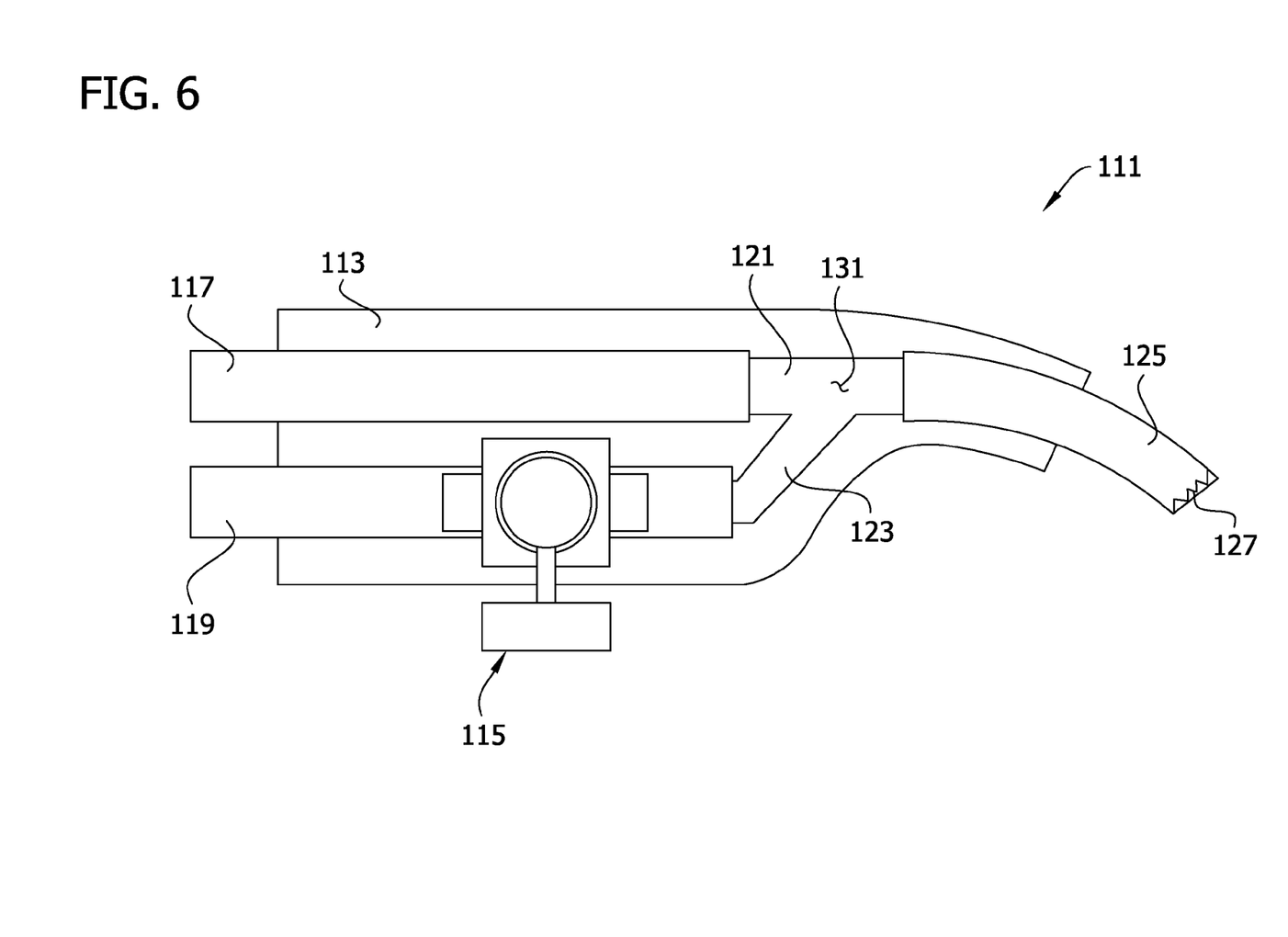
FIG. 6 is a schematic of a second embodiment of a suction wand.

A second embodiment of a suction wand 111 of the present invention is shown in FIG. 6. The wand 111 of the second embodiment comprises a handle 113 and a valve 115 partially received in the handle moveable between an open and closed position. In the illustrated embodiment, the valve 115 is a ball valve. In the open position, an inflow tube 117 can deliver positive pressure from a positive pressure source (not shown) to a positive pressure conduit 121 in the handle 113. The positive pressure conduit 121 extends through the handle 113 out a distal end of the handle to a tip portion 125. A filter screen 127 is disposed in an open, distal end of the tip portion 125. The wand 111 is configured to deliver a positive pressure force at the tip portion 125 of about 50 psi.

An outflow tube 119 extends through the handle 113 and connects to a suction conduit 123 in the handle. The suction conduit 123 also extends through the handle 123 and out the distal end of the handle to the tip portion 125. The positive pressure conduit 121 and suction conduit 123 converge in the handle 113 at a permanent Y-junction 131. In the closed position, the outflow tube 119 can create a negative pressure gradient at the tip portion 125 by activation of a suction source (not shown) in fluid communication with the outflow tube.

Figure 7:
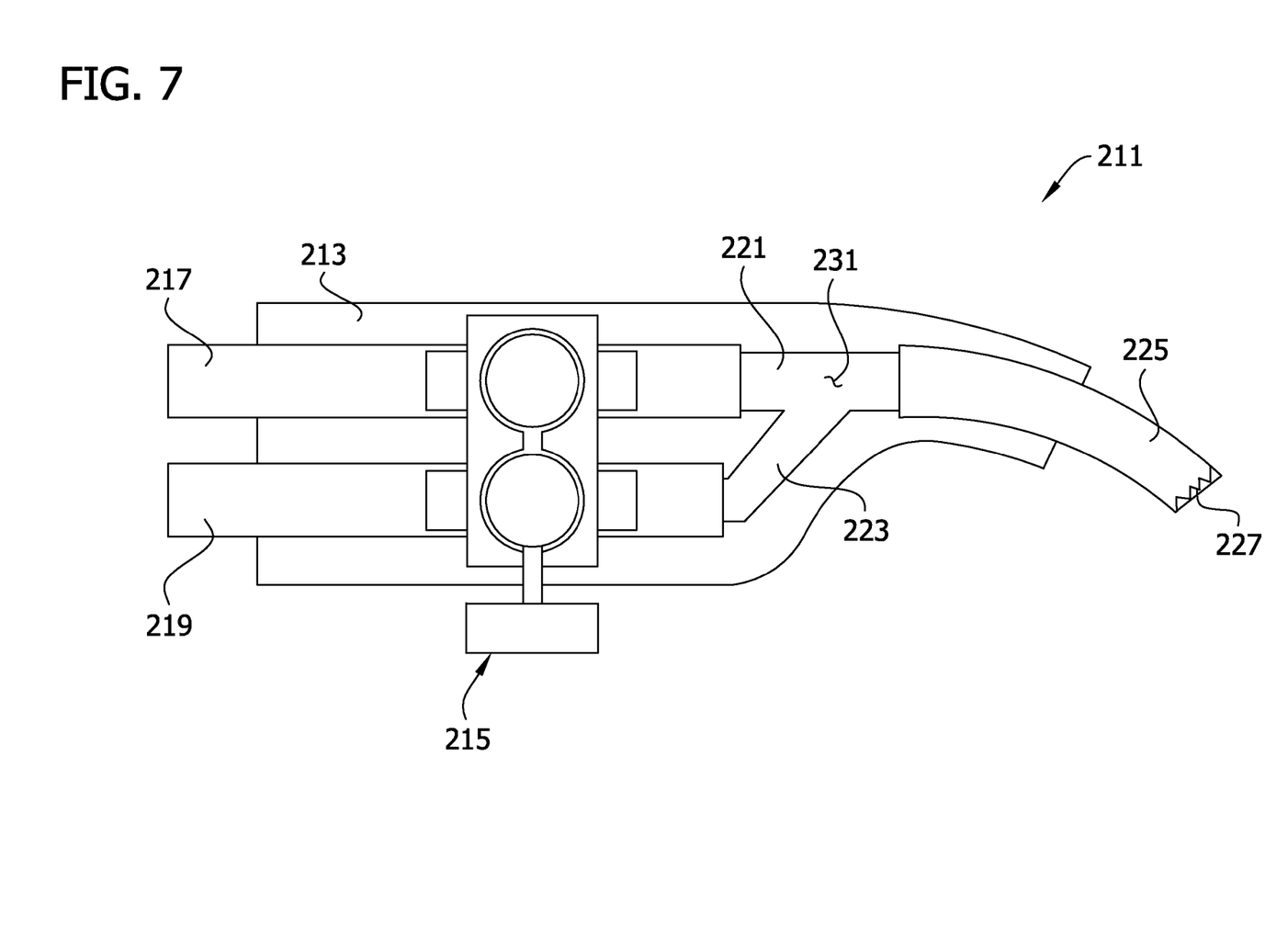
FIG. 7 is a schematic of a third embodiment of a suction wand.

A third embodiment of a suction wand 211 of the present invention is shown in FIG. 7. The third embodiment is substantially the same as the second embodiment except for valve 215 which is configured to control the delivery of pressure in both the suction conduit 223 and the positive pressure conduit 221. The valve 215 is configured such that in a first position the valve closes the positive pressure conduit 221 and opens the suction conduit 223. In a second position, the valve 215 closes the suction conduit 223 and opens the positive pressure conduit 221. In the illustrated embodiment, the valve 215 is a double-ball valve. However, other suitable valves can be used within the scope of the invention.

Figure 8:
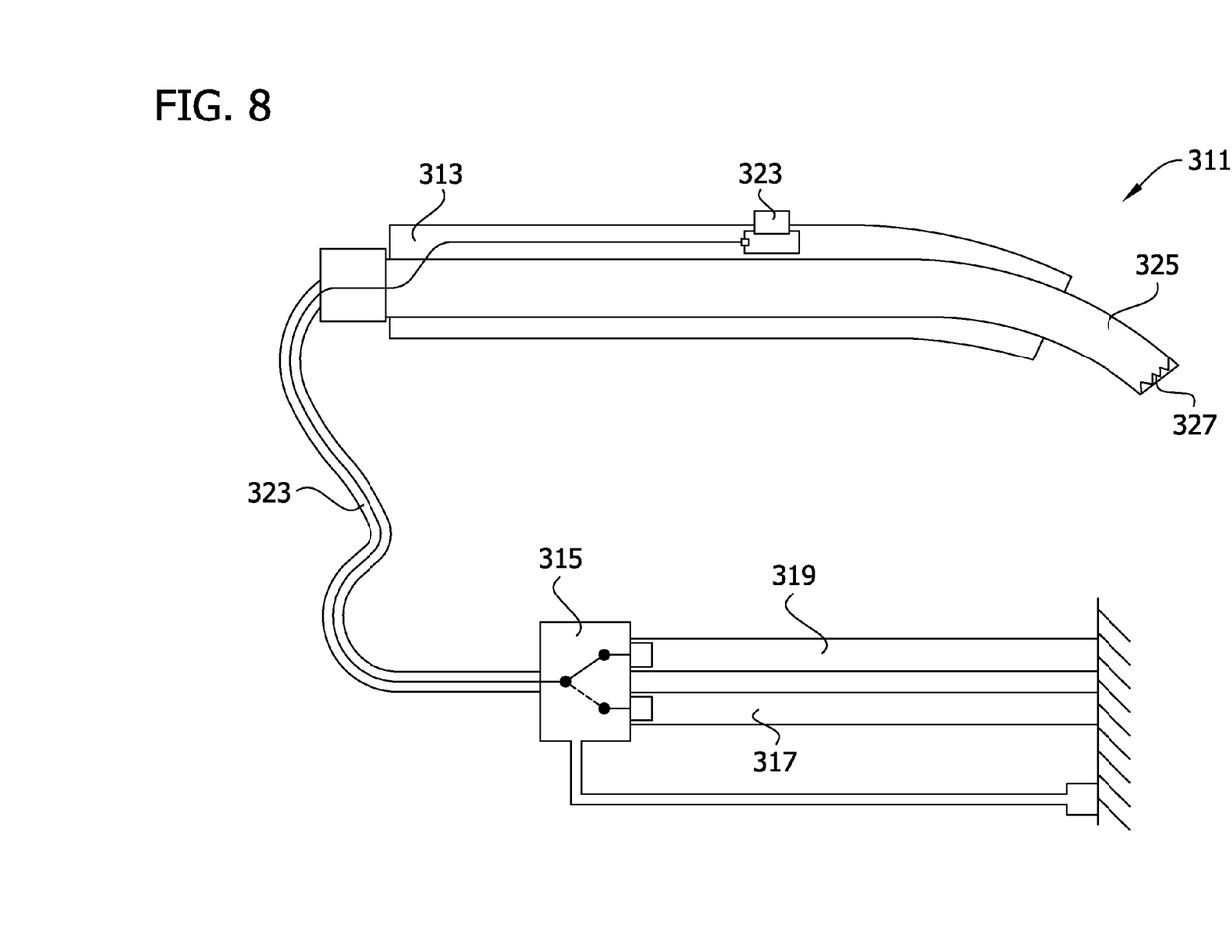
FIG. 8 is a schematic of a fourth embodiment of a suction wand.

A fourth embodiment of a suction wand 311 of the present invention is shown in FIG. 8. The wand 311 of the fourth embodiment comprises an inflow tube 317 and an outflow tube 319 adapted for connection to respective positive pressure and negative pressure sources. The tubes 317, 319 are connected to a switch 315 at their distal ends. A hose 323 extends from the switch and connects to a positive pressure/suction conduit 321 received in a handle 313 of the wand 311. A button 232 on the handle 313 is depressable to move the switch 315 between the inflow and outflow tubes 317, 319 to selectively communicate one of the tubes with the hose 232. A tip portion 325 extends from a distal end of the handle 313 and has a filter screen 327 disposed in an open distal end. This embodiment is similarly configured to generate a positive pressure force of about 50 psi at the open distal end of the tip portion 325.

Figure 9:
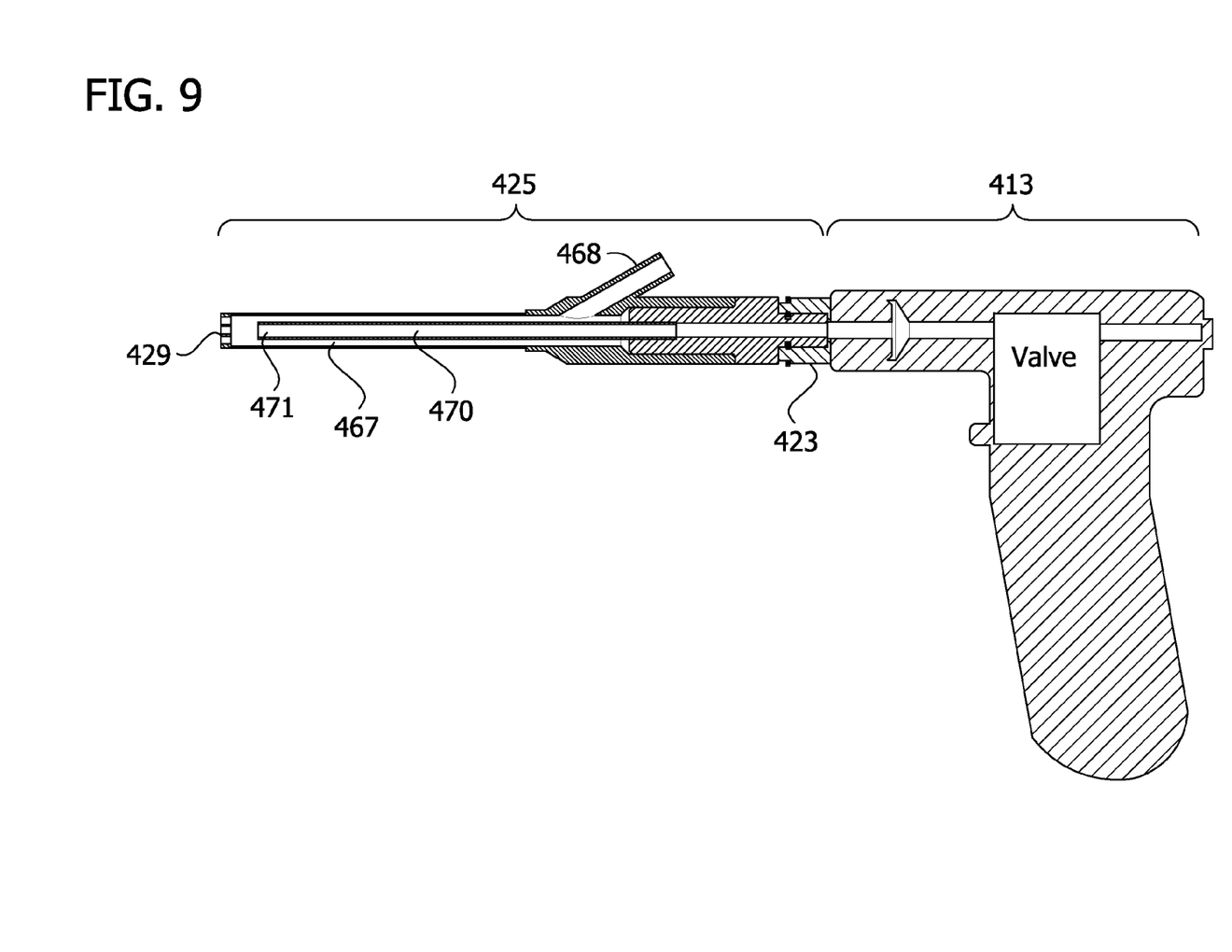
FIG. 9 is a schematic of a fifth embodiment of the suction wand.

A further embodiment of the suction wand is shown in FIG. 9. This embodiment includes a handle portion 413 connected to a head portion 425 at a connector 423. Similar to the embodiment in FIGS. 1-3, the head portion 425 includes a tubular member and a suction tip at 429. As with the embodiment of FIGS. 1-2, the interior space 467 of the head portion and the suction lead 468 define a suction conduit which partially defines a suction path extending from a free end of the suction conduit at the suction tip 429 remote from the handle back through the head portion and to a vacuum source end of the suction path remote from the suction tip. Distinct from FIGS. 1-3, in this embodiment the suction path does not pass through the handle 413. As with FIGS. 1-3, in this embodiment there is a positive pressure conduit comprising the extension at 470 and it is at least partially disposed in the head portion and partially defines a fluid path through which fluid flows and is directed into the suction conduit at the positive pressure conduit tip at 471 in a direction toward the tip 429 such that fluid flows in the tip direction for expelling debris from the tip. Preferably there is a screen as previously described in connection with FIGS. 5A and 5B at the tip 429. Upon activation of positive pressure through the positive pressure conduit, a burst of positive pressure fluid, preferably $CO_2$, is directed at the back side of the filter screen to expel debris from the filter screen.

The embodiment in FIG. 9 also shows that the positive pressure conduit has a longitudinal axis which is coincident with a longitudinal axis of the suction path along a majority of the length of the tubular member of the head portion. In particular, there is a positive pressure conduit at least partially disposed in the head portion and partially defining a fluid path. Fluid flows through this positive pressure conduit and is directed into the suction conduit in a direction toward the tip such that fluid flows in the tip direction for expelling debris from the tip. It can be seen that the positive pressure conduit has a longitudinal axis which is coincident or parallel with a longitudinal axis of the suction path along a majority of the length of the tubular member of the head portion. There is a conduit valve operable between an open position in which fluid flows through the positive pressure conduit and into the suction conduit toward the suction tip and a closed position in which fluid does not flow into the suction conduit. This is in agreement with the embodiment in FIGS. 1-3. These axes—the axis of the positive pressure conduit and of the suction conduit—may alternatively be parallel, rather than coincidental. It is also seen that the positive pressure conduit longitudinal axis is coincident (or alternatively may be parallel) with a longitudinal axis of the tubular member of the head portion from the connection 423 between the handle and the head portion in the tip direction. The suction path, as in the other embodiments, surrounds the positive pressure conduit along a majority of the length of the tubular member of the head portion.

In a variation of the above embodiments, the suction tip has the shape of a surgical dissector and can be used to retract, manipulate, and expose tissues of the surgical wound.

The invention encompasses relative arrangement of the suction conduit and positive pressure conduit as described herein and is not narrowly limited to a suction wand of any particular absolute dimensions. The wand may be configured so the suction tube in the head portion and at the tip is relatively wider to increase suction flow. Or the suction tube may be very thin such as only 3 or 4 mm in its widest dimension at the suction tip, as is applicable for more precise applications such as neurosurgery.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions without departing from the scope of the invention, it is intended that all matter contained in the above description and shown in the accompanying drawings shall be interpreted as illustrative and not in a limiting sense.

What is claimed is:

1. A suction wand for use in aspirating a surgical site during a surgical operation involving cutting of tissue which yields debris, the suction wand comprising:
   a handle;
   a head portion attached to the handle at a connection, wherein the head portion comprises a tubular member;
   a suction conduit at least partially disposed in the head portion and partially defining a suction path;
   a suction tip at a free end of the suction conduit remote from the handle, wherein the suction path extends from the suction tip to a vacuum source end of the suction path remote from the suction tip;
   a filter screen for retaining debris, wherein the filter screen comprises a surface with holes perforated therein and is disposed in the suction path at the suction tip and has a first side facing a tip direction and an opposite second side facing a vacuum source direction;
   a positive pressure conduit in the head portion through which fluid flows and is directed into the suction conduit in a direction toward the tip such that fluid flows in the tip direction for expelling debris from the tip; and
   a conduit valve operable between an open position in which fluid flows through the positive pressure conduit and into the suction conduit toward the suction tip and a closed position in which fluid does not flow into the suction conduit;
   wherein the positive pressure conduit has a longitudinal axis which is coincident with a longitudinal axis of the suction path along a majority of the length of the tubular member of the head portion.

2. The suction wand of claim 1 wherein the surface of the screen is flush with the tip.

3. The suction wand of claim 1 wherein the surface of the screen is slightly inset from the plane of the tip.

4. The suction wand of claim 1 wherein the screen has a ratio of the total entrance area of holes to solid area on the screen between 0.2 and 0.6.

5. The suction wand of claim 4 wherein the screen has a ratio of the total entrance area of holes to total area of between 0.4 and 1.

6. A suction wand for use in aspirating a surgical site during a surgical operation involving cutting of tissue which yields debris, the suction wand comprising:
   a handle;
   a head portion attached to the handle at a connection, wherein the head portion comprises a tubular member;
   a suction conduit at least partially disposed in the head portion and partially defining a suction path;
   a suction tip at a free end of the suction conduit remote from the handle, wherein the suction path extends from the suction tip to a vacuum source end of the suction path remote from the suction tip;
   a filter screen for retaining debris, wherein the filter screen comprises a surface with holes perforated therein and is disposed in the suction path at the suction tip and has a first side facing a tip direction and an opposite second side facing a vacuum source direction;
   a positive pressure conduit in the head portion through which fluid flows and is directed into the suction conduit in a direction toward the tip such that fluid flows in the tip direction for expelling debris from the tip; and
   a conduit valve operable between an open position in which fluid flows through the positive pressure conduit and into the suction conduit toward the suction tip and a closed position in which fluid does not flow into the suction conduit, wherein
   the positive pressure conduit has a longitudinal axis which is coincident or parallel with a longitudinal axis of the suction path and is disposed within the suction conduit along the majority of the length of the tubular member of the head portion.

7. The suction wand of claim 1 wherein the wherein the positive pressure conduit and the suction conduit define distinct lumens.

8. The suction wand of claim 1 wherein a portion of the positive pressure conduit is fixed within the tubular member of the head portion in spaced apart alignment with the filter screen.

9. The suction wand of claim 8 wherein the portion of the positive pressure conduit is fixed within the tubular member of the head portion such that the longitudinal axis of the positive pressure conduit along the portion is fixedly oriented substantially orthogonally to surface of the filter screen.

10. The suction wand of claim 1 wherein the conduit valve comprises an actuator, the actuator being disposed on the handle.

11. The suction wand of claim 1 wherein the head portion connects to the handle at a distal end of the handle and extends distally away from the handle.

* * * * *